United States Patent [19]

Goff et al.

[11] Patent Number: 4,896,965

[45] Date of Patent: Jan. 30, 1990

[54] REAL-TIME ALKALI MONITORING SYSTEM

[75] Inventors: David R. Goff, Christiansburg, Va.; Robert R. Romanosky, Prosperity, Pa.; Peter Hensel, Morgantown, W. Va.

[73] Assignee: The United States of America as represented by the United States Department of Energy, Washington, D.C.

[21] Appl. No.: 244,759

[22] Filed: Sep. 14, 1988

[51] Int. Cl.$^4$ .......................................... G01N 21/72
[52] U.S. Cl. .................................... 356/417; 356/307; 250/554
[58] Field of Search ...................... 356/307, 315, 417; 250/227, 554

[56] References Cited

U.S. PATENT DOCUMENTS 4,616,137 10/1986 Goff et al. .......................... 250/227

Primary Examiner—F. L. Evans
Attorney, Agent, or Firm—Stephen D. Hamel; Earl L. Larcher; William R. Moser

[57] ABSTRACT

A fiber optics based optical emission line monitoring system is provided in which selected spectral emission lines, such as the sodium emission line, may be detected in the presence of interfering background radiation. A combustion flame is fed by a diverted portion of a process stream and the common end of a bifurcated or quadfurcated fiber optic light guide is adapted to collect light from the flame. The light is guided through the branches of the fiber optic cable to bandpass filters, one of which is adapted to each of the branches of the fiber optic light guide. The bandpass filters are centered at wavelengths corresponding to the emission lines to be detected and two separate filters are required for each species being detected. The first filter has a bandwidth of about 3 nms and the second filter has a bandwidth of about 10 nms. Light detectors are located to view the light passing through the bandpass filters and amplifiers are connected to receive signals from the light detectors. The amplifier corresponding to the bandpass filter having the narrower bandwidth is preset to scale the signal by a factor equal to the ratio of the wide and narrow bandwidths of the bandpass filters. This scaling produces a scaled signal from which the difference between the scaled signal on the other signal can be calculated to produce a signal having an amplitude directly proportional to the concentration of the species of interest and independent of background radiation.

21 Claims, 4 Drawing Sheets

REAL-TIME ALKALI MONITORING SYSTEM

FIELD OF THE INVENTION

The present invention relates to an alkali monitoring system capable of extractive, real-time alkali concentration measurements in process streams.

BACKGROUND OF THE INVENTION

The alkali contents of process streams and particularly coal-derived gaseous fuels and their products of combustion, are important parameters to accurately assess due to their potential for corrosion and erosion of downstream components, such as gas turbines, in hot environments. Current industrial standards for turbine fuels require less than 70 parts per billion (ppb) of alkali for 1,340 Kcal/m$^3$ fuel gas and one ppm by weight for particles in the gas fed into the turbine. After an extensive study corrolating alkali concentration with turbine-blade wear, it has been determined that to achieve 25,000 hours of use (an acceptable lifetime) from a gas turbine, the level of alkali in the fuel stream should not exceed 24 ppb. In order to assess if fuel gases are meeting gas turbine and other component standards, analytical methods are required for the measurement of alkali concentration in high-temperature process streams.

Typically, alkali measurements in process streams are made by laboratory analysis of sodium and potassium content of particles which are collected by filters. Also, alkali measurements are made by laboratory analysis of the sodium and potassium content of condensates which are collected by impinger trains from the gas streams. Both methods require long sampling periods of between four and eight hours and generate only a time-averaged value. These methods cannot provide information important to assess short-term, transient behavior of alkali loadings in the system. It is important to assess these short-term loadings by real-time analysis due to their damage potential to downstream units and because of their role in determining process stability or diagnosing process instability. Further, assessment of short-term loadings is important in order to take corrective action if the alkali levels exceed component standards. In addition, to accurately assess the alkali content of fuel and exhaust streams at component specification levels, the alkali monitoring technique must also possess detection limits in the part per billion concentration range. A wide dynamic range is also an essential attribute so that streams containing both part per billion and part per million levels can be monitored, and to allow for fast, accurate tracking of transient alkali behavior. In order to respond to this need for real-time transient alkali data often at low part per billion levels, a number of techniques have been recently investigated. A hot wire ionization monitor has been tested on a fluidized-bed combuster. This technique determines alkali levels by measuring the current generated upon alkali impaction and subsequent ionization on a platinum wire positioned in the gas stream. However, it was shown in preliminary tests that quantitative information on alkali content of process streams was not achievable.

Another in situ alkali monitoring device is being developed which utilizes laser-induced photoionization spectroscopy to identify gas-phase alkali species. Alkali speciation is possible using this technique, although its application to routine-on-line process stream analyses is uncertain due to its expense and potential calibration problems.

A flame emission alkali monitor system composed of a burner, a light collection system, and a computer-controlled, dual-channel spectrometer has also been developed. In this device, a sample of a gas stream is introduced into the flame produced by the burner which is fueled with either an oxygen-hydrogen or nitrous oxide-acetylene mixture. The alkali containing species are vaporized, and the alkali atoms are thermally excited. The intensities of the sodium and potassium emission lines are measured simultaneously by two 0.25 meter focal length monochromators. This analyzer yields an on-line measurement every one to five minutes and has been successfully tested at various gasification and fluidized-bed combustion facilities.

Based on the flame atomic emission technique, an extractive, total (vapor and particle-bound) sodium and potassium monitor has been designed, constructed and tested. This monitor is described in U.S. Pat. No. 4,616,137 issued on Oct. 7, 1986. In that system, alkali flame emissions are focused on one branch of a bifurcated fiber optic cable and guided to a first bandpass filter adapted to the common trunk end of the cable. A portion of the light is allowed to pass through the filter to a first detector and the remaining light is reflected back through the common trunk portion of the fiber to a second bandpass filter adapted to the end of the other branch of the cable. The first filter is centered at a wavelength corresponding to the emission line with a small bandwidth. The second filter is centered at the same wavelength but has a larger bandwidth. Two light detectors are located to view the light passing through the filters. The second detector is blind to light corresponding to the emission line of interest which is detected by the first detector and the difference between the two detector outputs is used to determine the intensity of the combustion flame emission of interest.

The system described in U.S. Pat. No. 4,616,137 is relatively inflexible and cannot be easily adapted to detecting two or more alkali species simultaneously. In addition, it relies on an estimate of the background radiation that falls within the spectral region of interest thus creating a potential for uncertainty in the measurements from the system.

Accordingly, there is a need in the art for a real-time alkali monitoring system which is capable of accurately assessing alkali concentration in process streams.

SUMMARY OF THE INVENTION

The present invention relates to a real-time alkali monitoring system for detecting selected alkali emissions from a light source in the presence of interfering background radiation. In one embodiment, the system employs a bifurcated fiber optic cable having first and second branches attached to a common trunk and adapted at the common end to optically couple light from a light source to the cable. First and second bandpass optical filters having a passband centered about a selected emission line are disposed at the ends of each of the branches of the cable. The first bandpass filter has a bandwidth at least as wide as the selected emission line and the second bandpass filter has a bandwidth substantially wider than the bandwidth of the first bandpass filter. The system also includes a pair of light detector means adapted to intercept light transmitted by each of the bandpass filters. Finally, the system includes a means for scaling one of the output signals from the detectors and a means for calculating the difference between the scaled output signal and the other output signal to generate a third output signal having an amplitude proportional to the intensity of the emission line being monitored.

In a second embodiment, the system includes a pair of beam splitters located at the ends of the branches of the fiber optic cable between the cable and the bandpass filters. In this embodiment, the system includes four bandpass filters and is capable of monitoring two different alkali species simultaneously by employing each branch of the fiber optic cable as a separate monitoring system.

In a third embodiment of the invention, a quadfurcated fiber optic cable is employed. A bandpass filter is located at each of the four branches of the quadfurcated fiber optic cable. In this embodiment, it is also possible to monitor two alkali species simultaneously since only two branches of the cable are required to monitor a single species. The species monitoring is accomplished in the same manner as the first embodiment of the invention.

Finally, the present invention also encompasses a method of real-time monitoring of alkali concentrations in process streams. The method involves diverting a sample from a process stream to a combustion burner and combusting the sample to produce flame emissions. The flame emissions are then transmitted to a pair of bandpass filters having passbands centered about the spectral-emission line of an alkali species, the first bandpass filter having a bandwidth at least as wide as the selected emission line and the second bandpass filter having a bandwidth substantially wider than the bandwidth of the first bandpass filter. The signals transmitted by each of the bandpass filters are then detected and one of the detected signals is scaled. Finally, the difference between the scaled signal and the other detected signal is calculated to produce an output signal having an amplitude proportional to the intensity of the emission line being monitored.

It is the primary object of the present invention to provide an alkali monitor which is rugged, portable, compact and highly-sensitive.

It is a further object of the present invention to provide an alkali monitor capable of generating real-time data over a wide dynamic range.

It is a still further object of the present invention to provide an alkali monitor which can monitor two or more alkali species simultaneously.

These and other objects of the present invention will be apparent to one of ordinary skill in the art from the detailed description which follows.

DETAILED DESCRIPTION OF THE PREFERRED EMBODIMENTS

Figure 1:
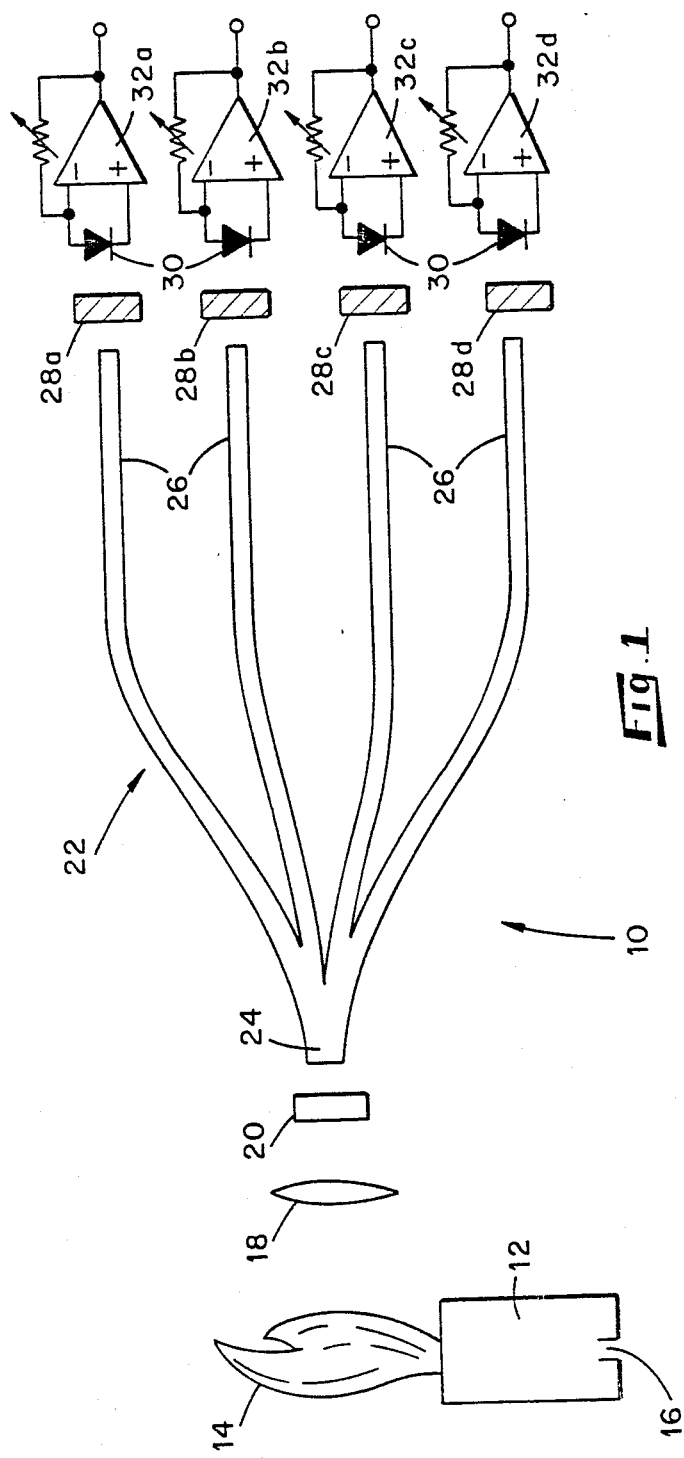
FIG. 1 is a schematic representation of an alkali monitoring system employing a quadfurcated fiber optic cable in accordance with the present invention.

Referring now to FIG. 1, there is shown an alkali monitoring system 10. The system employs a combustion burner 12 having a flame 14 and a sample inlet 16. Sample gas is fed to combustion burner 12 through sample inlet 16 and combusted in flame 14. The flame is preferably a non-cooled nitrous oxide/acetylene flame. The combustion causes any alkali in the sample to give off its characteristic emission in the center portion of flame 14. Combustion burner 12 is preferably designed to be low-cost, easy to construct, rugged, and able to withstand temperatures of 1,000° F. with no adverse effects. This is important in process situations where sample integrity is required since temperature differences between the process stream, sample inlet 16 and combustion burner 12 could result in erroneous data.

The next element in alkali monitoring system 10 is lens 18 located between flame 14 and opal diffuser 20. Lens 18 increases the light gathering efficiency of alkali monitoring system 10 from flame 14. Lens 18 may be any suitable lens for increasing light gathering efficiency known to those of ordinary skill in the art. Opal diffuser 20 improves the illumination uniformity at common end 24 of fiber optic cable 22. Without opal diffuser 20, the light-splitting ratio between the branches of fiber optic cable 22 will change slightly if the illuminating angle is changed. Opal diffuser 20 tends to improve the illumination uniformity, thus, stabilizing the splitting ratio among the fiber optic branches.

Light from flame 14 is gathered by lens 18 and transmitted via opal diffuser 20 to common end 24 of fiber optic cable 22. Fiber optic cable 22 is shown as a quadfurcated fiber optic cable including common end 24 and branches 26. The quadfurcated fiber optic cable 22 preferably has a 3/16" diameter aperture on common end 24. Common end 24 has fibers randomly organized and fiber optic cable 22 preferably has a total length of about 3 feet. The purpose of fiber optic cable 22 is to allow sensitive detector elements and electronics to be spacially separated from flame 14. Fiber optic cable 22 also provides a convenient method of allowing four different detectors to analyze light from a common collection point.

The light that exits each of the four branches 26 of fiber optic cable 22 is transmitted to four dichroic bandpass filters 28a–d. Each of bandpass filters 28a–d has a different combination of passband central wavelength and bandwidth.

Bandpass filters 28a–b are employed to determine the concentration of one alkali species whereas bandpass filters 28c–d are set to determine alkali concentration of a second alkali species. Thus, bandpass filters 28a and 28b have nominal passband central wavelengths centered on the characteristic emission wavelength of a first alkali species. Bandpass filters 28c–d have a nominal passband central wavelength equivalent to the characteristic emission wavelength of a second alkali species. Bandpass filters 28a and 28c each have bandwidths which are at least as wide as the emission line of the alkali species being detected. Bandpass filters 28b and 28d each have bandwidths substantially wider than the bandwidths of bandpass filters 28a and 28c respectively. For example, filters 28a and 28c can have a full width half-maximum of three nms whereas bandpass filters 28b and 28d may have a full width half-maximum of 10 nms.

The outputs of bandpass filters 28a–d impinge upon detectors 30. Detectors 30 are preferably Hamamatsu photodiodes. Preferably, special detectors are chosen for each species of alkali being detected. For example, if sodium is being detected, gallium arsenide phosphide detectors type G1737 are used. These detectors are chosen because they are only sensitive to visible radiation and thus error caused by infrared radiation leakage through bandpass filters 28a–d can be eliminated.

If potassium is being monitored, silicon photodiodes type S1336-8BK are employed. These detectors are sensitive to light from the near ultraviolet to the near infrared range and thus encompass the emission line of potassium. Both detector types offer exceptional dark current, noise equivalent power and responsivity specifications. The most preferred detector performance is summarized in Table 1.

TABLE 1

Detector Performance

| Type | Wavelength Response | Dark Current[1] | Shunt Resistance[2] | NEP | Area |
|---|---|---|---|---|---|
| Silicon | 320–1100 nm | 150 pA | 0.3GΩ | $2 \times 10^{-14}$ w/$\sqrt{HZ}$ | 33 mm² |
| GaAsP | 400–760 nm | 10 pA | 5.0GΩ | $7 \times 10^{-15}$ w/$\sqrt{HZ}$ | 29.3 mm² |

[1] At a reverse voltage of 10 mV at room temperature (25° C.). Actual offset during operating conditions is typically less than 0.25 mV.
[2] At room temperature (25° C.), typical.

Each detector 30 converts the light transmitted to it into an output signal. These output signals are conveyed to amplifiers 32a–d. Amplifiers 32a–d are chosen primarily for stability, low noise, and extremely low bias currents. These amplifiers are op amps and the preferred op amp is a Burr-Brown Op A111BM. This op amp offers exceptional stability, low noise and low-bias currents.

The amplifiers preferably have three selectable course gains of $2 \times 10^7$ V/A, $2 \times 10^8$ V/A, and $2 \times 10^9$ V/A. Amplifiers 32a and c are configured to output a signal which is scaled by a scaling factor with respect to the signal outputted by amplifiers 32b and 32d. The scaling factor is chosen to produce an output which can be used to separate the background noise from the alkali emission.

The outputs of the photodiodes are treated in a manner that allows background noise to be subtracted. The technique makes the assumption that the undesired background radiation is a linear function of wavelength over the ±5 nm region around the desired emission line. To show how the technique works, assume that the bandpass filters have 100 percent transmission in the passband and 0 percent emission in the out-of-band region. Assume that lambda is the wavelength of the desired emission line and $W_1$ and $W_2$ are the widths of the filter passbands. Also assume that the emission line is centered in the passband of both filters. Equation 1 gives the Equation for the undesired background radiation.

$$B(\lambda) = A_1\lambda + B_1 \tag{1}$$

The passbands of the two filters F1 and F2 are defined in Equations 2 and 3.

$$F_1(\lambda) = 1.0 \text{ for } (\lambda_1 - W_1/2) \leq \lambda \leq (\lambda_1 + W_1/2) \tag{2}$$

$$F_1(\lambda) = 0.0 \text{ for } \lambda < (\lambda_1 - W_1/2) \text{ or } \lambda > (\lambda_1 + W_1/2)$$

$$F_2(\lambda) = 1.0 \text{ for } (\lambda_1 - W_2/2) \leq \lambda \leq (\lambda_1 + W_2/2) \tag{3}$$

$$F_2(\lambda) = 0.0 \text{ for } \lambda < (\lambda_1 - W_1/2) \text{ or } \lambda > (\lambda_1 + W_2/2)$$

The intensity of the emission line is given by Equation 4.

$$I_1(\lambda) = I_o \text{ for } \lambda = \lambda_1 \tag{4}$$

$$I_1(\lambda) = 0.0 \text{ for } \lambda \neq \lambda_1$$

If one now adds the intensity of the emission line and the background and integrates over the filter passband regions, one obtains light intensities L1 and L2 as shown below.

$$L_1 = I_o + \int_{\lambda_1 - \frac{W_1}{2}}^{\lambda_1 + \frac{W_1}{2}} (A_1\lambda + B_1) d\lambda \tag{5}$$

$$L_2 = I_o + \int_{\lambda_2 - \frac{W_2}{2}}^{\lambda_2 + \frac{W_2}{2}} (A_1\lambda + B_1) d\lambda \tag{6}$$

Equations 5 and 6 may be integrated and reduced to Equations 7 and 8 below.

$$L_1 = A_1\lambda_1 W_1 + B_1 W_1 + I_o \tag{7}$$

$$L_2 = A_1\lambda_1 W_2 + B_1 W_2 + I_o \tag{8}$$

Now, if Equation 7 is scaled by a factor equal to ($W_2/W_1$), one obtains Equation 9.

$$L_1 = A_1\lambda_1 W_2 + B_1 W_2 + I_o(W_2/W_1) \tag{9}$$

Now subtract Equation 8 from Equation 9 to obtain Equation 10.

$$L_1 - L_2 = I_o \left[ \frac{W_2 - W_1}{W_1} \right] \tag{10}$$

Thus, by merely applying a gain factor of $W_2/W_1$ to one of the detector outputs and subtracting the two outputs from one another, a signal is obtained that is solely due to the desired emission line regardless of the intensity or slope of the background radiation. It can be seen from Equation 10 that the widths of the passbands of bandpass filters 28a and 28c must be somewhat different from the widths of the passbands of bandpass filters 28b and 28d. A ratio of bandpass filter width of 3.1 is considered to be near optimum. This would allow a large percentage of the emission line intensity to be retained after background cancellation while ensuring (for most alkali emission lines) that only one emission line would be present in each filter's passband.

In practice, the instrument is first exposed to pure black body radiation, the gains are adjusted in the transimpedance amplifiers so that the outputs of the two channels are equal. The two outputs are then subtracted by an differential amplifier. The resultant difference is proportional to only the emission line and is independent of background radiation.

The instrument shown in FIG. 1 can be used with a bifurcated fiber optic cable to monitor a single alkali species at a time. Although this is a less preferred embodiment, it functions as well as the embodiment of FIG. 1 except that it only monitors a single alkali species at a time.

Figure 2:
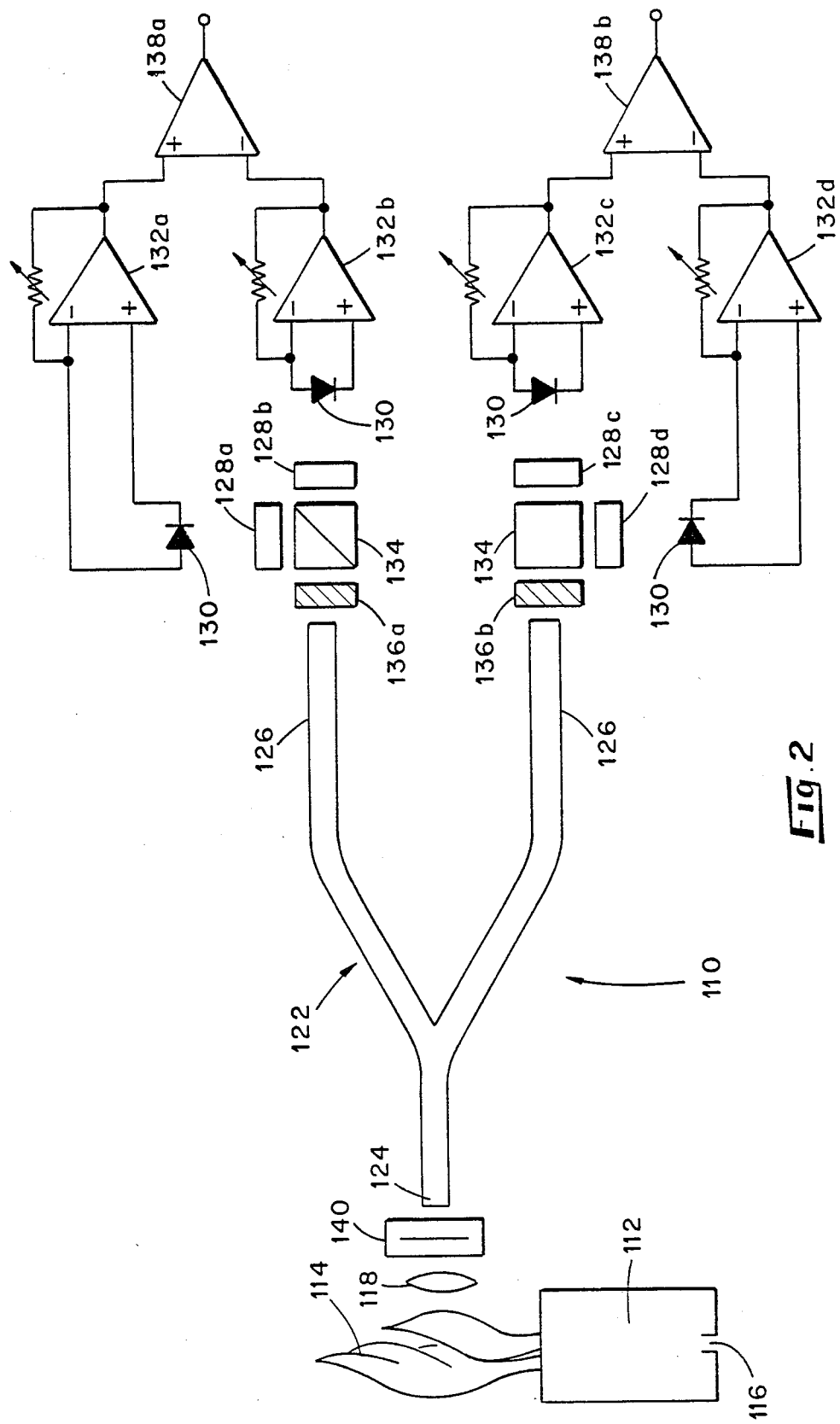
FIG. 2 is an illustration of a second embodiment of an alkali monitoring system employing a bifurcated fiber optic cable in accordance with the present invention.

Referring now to FIG. 2, there is shown an alternate embodiment of the present invention which employs a bifurcated fiber optic cable 122 and uses a pair of beam splitters 134 to produce four signals from two branches of fiber optic cable 122.

The embodiment shown in FIG. 2 shows an alkali monitoring system 110. Included in this system is a combustion burner 112, a flame 114 and a sample inlet 116. Light from flame 114 is collected by lens 118 and focused onto the common end 124 of bifurcated fiber optic cable 122. This light passes through an electronic shutter 140 provided to allow the detectors to be exposed to the light signal from the flame so that the electronics can be calibrated or the alkali emissions monitored, or be cut off from the flame signal to allow the offset of the electronics to be adjusted.

In the monitoring mode, the light is transmitted through common end 124 to branches 126 of fiber optic cable 122. Light from branches 126 is transmitted to colored glass filters 136a-b. Filter 136a is an optional piece of equipment which may be included in the apparatus to reduce the amount of stray light, that is, emissions that fall outside the bandwidth of filters 128a-b, that reaches the detectors. Filter 136b can similarly be used with filters 128c-d.

Further, light passes through filters 136a-b to beam splitters 134 which split the signal evenly and cause it to impinge on dichroic bandpass filters 128a-d. Bandpass filters 128a and 128b are used in combination to monitor the concentration of one alkali species, whereas bandpass filters 128c and 128d are used in combination to monitor the concentration of a second, different alkali species. Thus, in this embodiment each branch of fiber optic cable 122 conveys a signal which is used for monitoring the concentration of a different alkali species.

The remainder of the apparatus in FIG. 2 is similar to that shown in FIG. 1 and operates in the same manner. The apparatus includes four photodiode detectors 130 and four amplifiers 132a-d. Amplifiers 132a and 132d are preset to apply a scaling factor to the signal received from detectors 130. More particularly, amplifier 132a will scale the signal received from detector 130 by a factor equivalent to the ratio of the bandwidths of bandpass filters 128a and 128b. In a similar manner, amplifier 132c will scale the signal received from detector 130 by a factor equivalent to the ratio of bandwidths between bandpass filter 128c and bandpass filter 128d.

Finally, the difference between the scaled output from amplifier 132a and the output from amplifier 132b is calculated to produce a signal having an amplitude proportional to the concentration of the alkali species being monitored by that channel of the apparatus. Also, the difference between the scaled output of amplifier 132c and the output of amplifier 132d is calculated to produce a signal having an amplitude proportional to the concentration of the alkali species being monitored by that channel of the apparatus. The differences can be calculated either by computer software programs or by hardware such as by differential amplifiers 138a-b which are known to those of ordinary skill in the art. For example, a suitable differential amplifier is disclosed in U.S. Pat. No. 4,616,137 which has been previously incorporated by reference herein. Differential amplifier 138a has a positive input connected to the output of amplifier 132a and a negative input connected to the output of amplifier 132b and functions by taking the difference between the outputs of amplifiers 132a and 132b to produce an output signal from differential amplifier 138a having an amplitude proportional to the intensity of the emission line of interest. Differential amplifier 138b operates in the same manner as differential amplifier 138a but it is connected to amplifiers 132c-d.

The signals from amplifiers 132 A-D and 32 A-D are preferably fed to an alkali monitor data system which includes at least one software program. The software includes six subroutines for calibration, data acquisition, valve status, flame out enable/disable, system parameters and manual tests.

The calibrate routine allows setting of the electronics offset (dark current) and channel balancing (flame zeroing). This operation is equivalent to zeroing out the system. Alkali standards can then be input into the system calibrate routine and can be stored for use in other routines. Calibrate also contains routines for retrieving previous calibration data, generating spline boundaries for curve fits, displaying curve fit coefficients, and plotting the calibration curves.

The data acquisition routine measures the alkali intensity of a sample, computes the alkali concentration via comparison to the calibration curves and plots the data to a display.

The other routines perform specialized system operation functions. Valve status allows the operator to open and close the burner and oxidant valves to the burner, the sample stream valve and cutoff filters 136. If the unit is to be unattended for a time, the operator can enable the flame and safety check, which closes the fuel and oxidant valves if it senses that the flame is extinguished for any reason.

System parameters is a routine that gives the operator the opportunity to modify the data sampling rate, modify sampling time constants and display all hardware settings. For diagnostic purposes, a manual test section is included that allows the operator to view different sections of the data collection process to determine where problems may be occurring. The performance of the alkali monitor of the present invention has been extensively characterized in laboratory tests with the use of alkali standards. Typical calibration curves for sodium and potassium have been generated and the reproducability of sodium and potassium data generated over a wide concentration range was typically ±5 to 10 percent. Currently, the lowest level of detection for sodium and potassium at a signal-to-noise ratio of 3 using this unit is approximately 500 parts per trillion. The highest concentration of alkali detectable by the present invention in undiluted sample stream is limited by the phenomenon of self-absorption of the analytical signal in the flame. Laboratory results indicate that 80 ppm sodium and 130 ppm potassium are the upper limits of concentration detectable by this unit before self-absorption phenomena are observed. Higher concentrations of alkali can be detected if dilution of the sample stream with nitrogen is performed. The following example of the invention is presented for illustration and description only.

EXAMPLE 1

Figure 3:
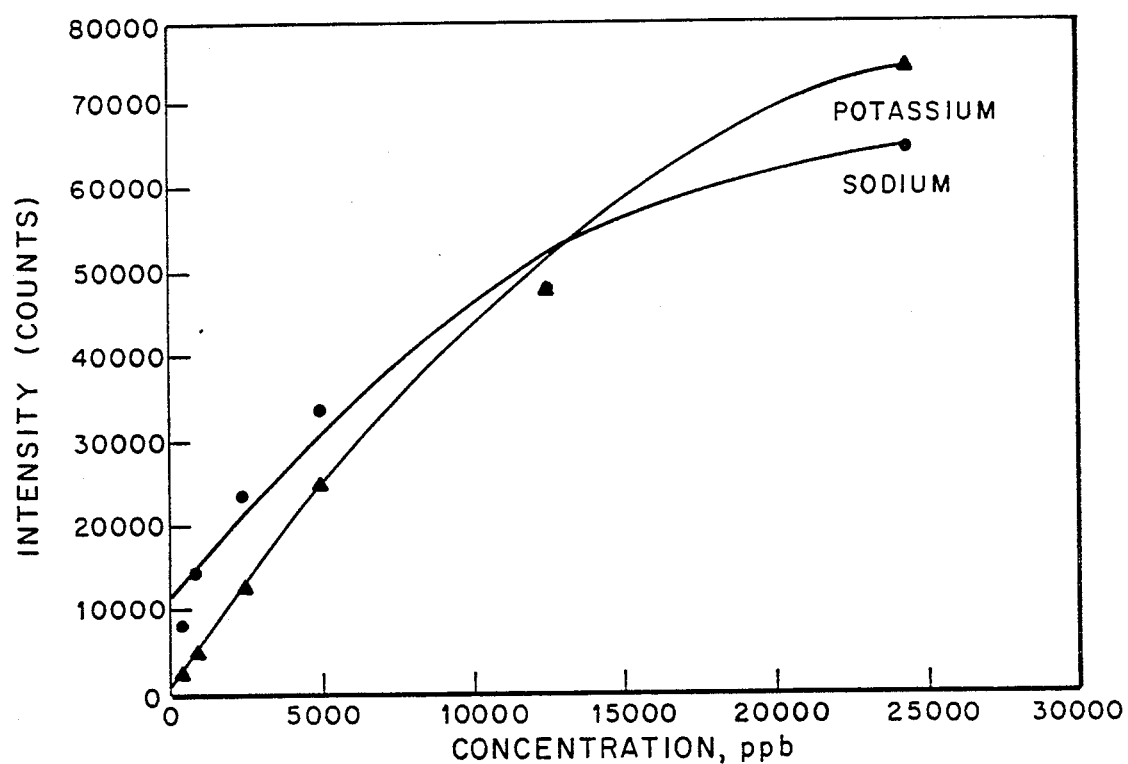
FIG. 3 is a calibration curve for sodium and potassium.

For the purposes of this example, calibration curves for sodium and potassium were developed over the range of concentrations between 0 and 25,000 ppb. These calibration curves were developed by feeding alkali-containing solutions of known concentration to the alkali monitor of the present invention. The calibration curves for sodium and potassium are shown in FIG. 3.

In order to generate the calibration curves, the alkali monitoring device of FIG. 1 was employed. Bandpass filter 28a had a full width half-maximum of 3 nms and had a nominal central wavelength of 589.0 nms., the characteristic emission wavelength for sodium. Bandpass filter 28b also had a nominal central wavelength of 589.0 nms and had a full width half-maximum of 10 nms. Bandpass filter 28c had a nominal central wavelength of 766.0 nms, the characteristic emission wavelength for potassium, and a full-width half-maximum of 3 nms. Bandpass filter 28d had a nominal central wavelength of 766.0 nms and a full-width half-maximum of 10 nms.

For the purposes of this example, amplifier 32a was set to scale its signal by a factor of 3.33 as was amplifier 32c.

Figure 4:
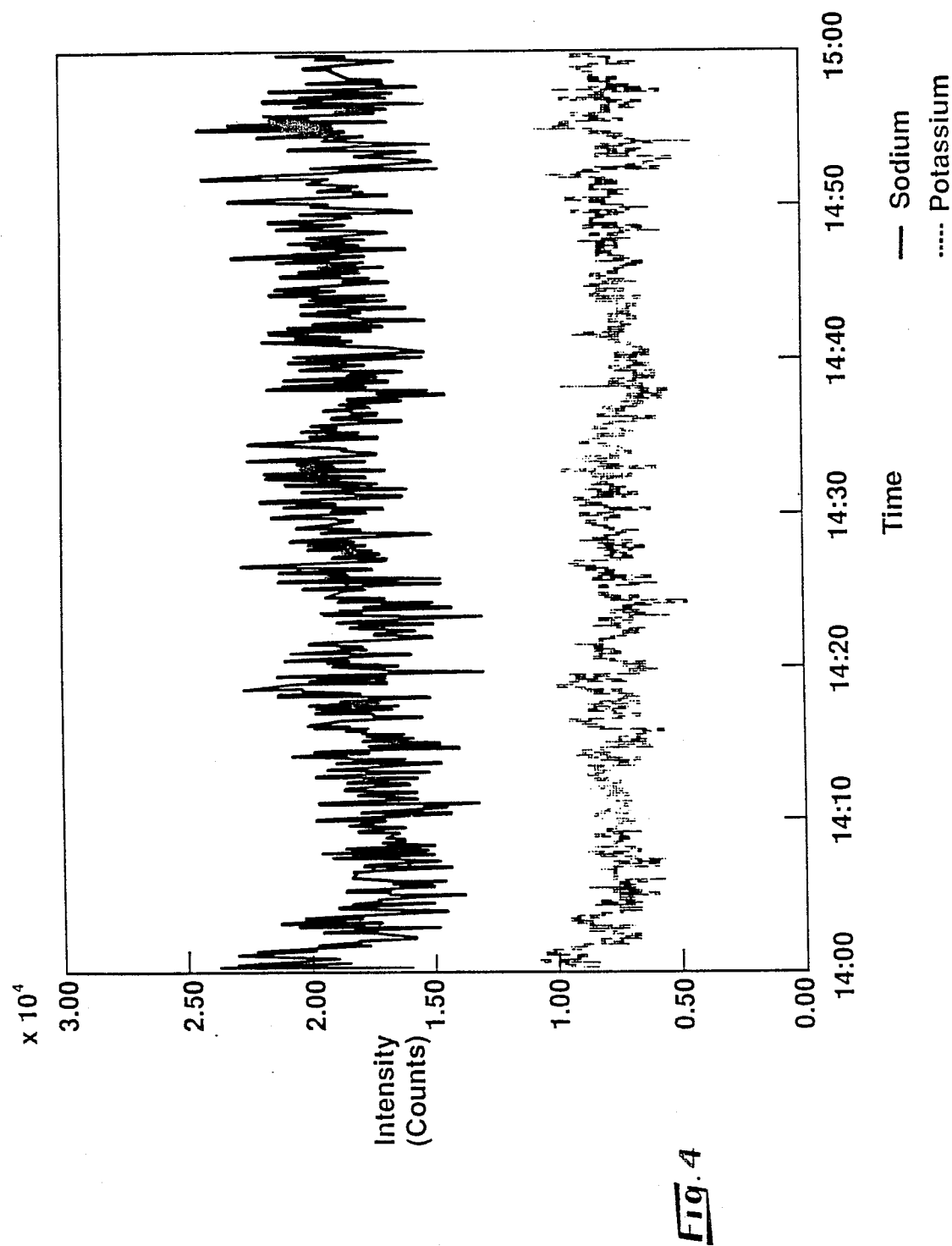
FIG. 4 is a response curve generated by the alkali monitor of the present invention for sodium and potassium.

An unknown process stream containing both sodium and potassium was then fed to the alkali monitoring device and a plot of the output intensity for sodium and potassium is shown in FIG. 4 over a one-minute time span. The data indicate a relatively constant rate of alkali release over the longer term consistent with the attainment of steady-state combustor conditions during this time period. A comparison of the output in FIG. 4 with the calibration curve in FIG. 3 shows that potassium concentrations were somewhere in the range of 2,500 to 3,000 ppb and sodium concentrations were in the range of about 500 ppb.

The foregoing description of embodiments of the invention has been presented for purposes of illustration and description. It is not intended to be exhaustive or to limit the invention to the precise forms disclosed, and many modifications and variations will be obvious to one of ordinary skill in the art in light of the above teachings. The scope of the invention is to be defined by the claims appended hereto.

We claim:

1. A real-time alkali monitoring system for detecting selected alkali emissions from a light source in the presence of interfering background radiation, comprising:
   a bifurcated fiber optic cable having first and second branches attached to a common trunk and adapted at the common end to optically couple light from a light source to said cable;
   a first bandpass optical filter having a passband centered about a selected emission line and a bandwidth at least as wide as the selected emission line and being disposed to intercept light passing from the end of said first branch of said cable;
   a second bandpass optical filter having a passband centered about a wavelength identical to that of said first bandpass filter and a bandwidth substantially wider than the bandwidth of said first bandpass filter and being disposed to intercept light passing from the end of said second branch of said cable;
   a first light detector means for generating a first signal having an amplitude proportional to the intensity of light transmitted through said first bandpass filter,
   a second light detector means for generating a second signal having an amplitude proportional to the intensity of light transmitted through said second bandpass filter;
   a means for scaling one of the output signals from said detectors; and,
   a means for calculating the difference between said scaled output signal and said other output signal to generate a third output signal having an amplitude proportional to the intensity of said emission line being monitored.

2. A system in accordance with claim 1 wherein said means for scaling comprises:
   a first variable gain amplifier connected to the output of said first light detector means and a second variable gain amplifier connected to the output of said second light detector means.

3. A system in accordance with claim 2 wherein said means for calculating comprises:
   a differential amplifier having a positive input connected to the output of said first variable gain amplifier and a negative input connected to the output of said second variable gain amplifier.

4. A system in accordance with claim 2 wherein the light source is a combustion flame.

5. A system in accordance with claim 2 further comprising:
   a lens means located between the light source and said common end of said cable for increasing the light gathering efficiency of the system.

6. A system in accordance with claim 5 further comprising:
   a diffuser means located between said lens means and said common end of said cable to improve the uniformity of illumination at said common end of said cable.

7. A system in accordance with claim 1 wherein said bandpass filters are dichroic filters having a passband centered about a wavelength selected from about 589 nm and about 766 nm.

8. A real-time alkali monitoring system for detecting two selected alkali emissions simultaneously from a light source in the presence of interfering background radiation, comprising:
   a bifurcated fiber optic cable having first and second branches attached to a common trunk and adapted at the common end to optically couple light from a light source to said cable;
   a first beam splitter disposed to intercept light passing from the end of said first branch of said cable and split the light into a first beam and a second beam;
   a second beam splitter disposed to intercept light passing from the end of said second branch of said cable and split the light into a third beam and a fourth beam;
   a first bandpass optical filter having a passband centered about a first selected emission line and having a bandwidth at least as wide as the first selected emission line and being disposed to intercept said first beam passing from said first beam splitter;
   a second bandpass optical filter having a passband centered about a wavelength identical to that of said first bandpass filter and a bandwidth substantially wider than the bandwidth of said first bandpass filter and being disposed to intercept said second beam passing from said first beam splitter;

a third bandpass optical filter having a passband centered about a second selected emission line and a bandwidth at least as wide as the second selected emission line and being disposed to intercept said third beam passing from said second beam splitter;

a fourth bandpass optical filter having a passband centered about a wavelength identical to that of said third bandpass filter and a bandwidth substantially wider than the bandwidth of said third bandpass filter and being disposed to intercept said fourth beam passing from said second beam splitter;

a first light detector means for generating a first signal having an amplitude proportional to the intensity of light transmitted through said first bandpass filter;

a second light detector means for generating a second signal having an amplitude proportional to the intensity of light transmitted through said second bandpass filter;

a third light detector means for generating a third signal having an amplitude proportional to the intensity of light transmitted through said third bandpass filter;

a fourth light detector means for generating a fourth signal having an amplitude proportional to the intensity of light transmitted through said fourth bandpass filter;

a means for scaling one of the output signals from said first and second detectors and one of the output signals from said third and fourth detectors, and a means for calculating the difference between said scaled output signal from said first and second detectors and the difference between said scaled output signal from said third and fourth detectors and said other output signal from said third and fourth detectors to generate fifth and sixth output signals each having an amplitude proportional to the intensity of one of said emission lines being monitored.

9. A system in accordance with claim 8 wherein said means for scaling comprises:

a first variable gain amplifier connected to the output of said first light detector means;

a second variable gain amplifier connected to the output of said second light detector means;

a third variable gain amplifier connected to the output of said third light detector means; and a fourth variable gain amplifier connected to the output of said fourth light detector means.

10. A system in accordance with claim 9 wherein said means for calculating comprises:

a first differential amplifier having a positive input connected to the output of said first variable gain amplifier and a negative input connected to the output of said second variable gain amplifier, and a second differential amplifier having a positive input connected to the output of said third variable gain amplifier and a negative input connected to the output of said fourth variable gain amplifier.

11. A system in accordance with claim 10 further comprising:

a first colored glass filter located between the end of said first branch of said cable and said first beam splitter to reduce the amount of stray light that reaches the said first and second detectors, and a second colored glass filter located between the end of said second branch of said cable and said second beam splitter to reduce the amount of stray light that reaches the said third and fourth detectors.

12. A system in accordance with claim 9 further comprising:

a lens means located between the light source and said common end of said cable for increasing the light gathering efficiency of the system.

13. A system in accordance with claim 12 further comprising:

a shutter means located between said lens means and said common end of said cable to allow illumination at said common end of said cable to be cut off.

14. A system in accordance with claim 9 wherein said bandpass filters are dichroic filters, and said first and second bandpass filters having a passband centered about a wavelength of about 589 nm, and said third and fourth bandpass filters having a passband centered about a wavelength of about 766 nm.

15. A real-time alkali monitoring system for detecting two different selected alkali emissions simultaneously from a light source in the presence of interfering background radiation comprising:

a quadfurcated fiber optic cable having first, second, third and fourth branches attached to a common trunk and adapted at the common end to optically couple light from a light source to said cable;

a first bandpass optical filter having a passband centered about a first selected emission line and having a bandwidth at least as wide as the first selected emission line and being diposed to intercept light passing from the end of said first branch of said cable;

a second bandpass optical filter having a passband centered about a wavelength identical to that of said first bandpass filter and a bandwidth substantially wider than the bandwidth of said first bandpass filter and being disposed to intercept light passing from the end of said second branch of said cable;

a third bandpass optical filter having a passband centered about a second selected emission line and having a bandwidth at least as wide as the second selected emission line and being disposed to intercept light passing from the end of said third branch of said cable;

a fourth bandpass optical filter having a passband centered about a wavelength identical to that of said third bandpass filter and a bandwidth substantially wider than the bandwidth of said third bandpass filter and being disposed to intercept light passing from the end of said fourth branch of said cable;

a first light detector means for generating a first signal having an amplitude proportional to the intensity of light transmitted through said first bandpass filter;

a second light detector means for generating a second signal having an amplitude proportional to the intensity of light transmitted through said second bandpass filter;

a third light detector means for generating a third signal having an amplitude proportional to the intensity of light transmitted through said third bandpass filter;

a fourth light detector means for generating a fourth signal having an amplitude proportional to the intensity of light transmitted through said fourth bandpass filter;

a means for scaling one of the output signals from said first and second detectors and one of the output signals from said third and fourth detectors, and a means for calculating the difference between said scaled output signal from said first and second detectors and said other output signal from said first and second detectors and the difference between said scaled other output signal from said third and fourth detectors and said output signal from said third and fourth detectors to generate fifth and sixth output signals each having an amplitude proportional to the intensity of respective of said first and second emission lines being monitored.

16. A system in accordance with claim 15 wherein said means for scaling comprises:
    a first variable gain amplifier connected to the output of said first light detector means,
    a second variable gain amplifier connected to the output of said second light detector means,
    a third variable gain amplifier connected to the output of said third light detector means, and
    a fourth variable gain amplifier connected to the output of said fourth light detector means.

17. A system in accordance with claim 16 wherein said means for calculating comprises:
    a first differential amplifier having a positive input connected to the output of said first variable gain amplifier and a negative input connected to the output of said second variable gain amplifier, and
    a second differential amplifier having a positive input connected to the output of said third variable gain amplifier and a negative input connected to the output of said fourth variable gain amplifier.

18. A system in accordance with claim 16 further comprising:
    a lens means located between the light source and said common end of said cable for increasing the light-gathering efficiency of the system.

19. A system in accordance with claim 18 further comprising:
    a diffuser means located between said lens means and said common end of said cable to improve the uniformity of illumination at said common end of said cable.

20. A system in accordance with claim 15 wherein said bandpass filters are dichroic filters and said first and second bandpass filters have a passband centered about a wavelength of about 589 nm and said third and fourth bandpass filters have a passband centered about a wavelength of about 766 nm.

21. A method for real-time monitoring of alkali concentrations in process streams, comprising:
    diverting a sample from a process stream to a combustion burner;
    combusting the sample to produce alkali flame emissions;
    transmitting the flame emissions to a pair of bandpass filters having passbands centered about the spectral emission line of an alkali species, the first bandpass filter having a bandwidth at least as wide as the selected emission line and the second bandpass filter having a bandwidth substantially wider than the bandwidth of the first bandpass filter;
    detecting the signals transmitted by each of the bandpass filters;
    scaling one of the detected signals, and
    calculating the difference between the scaled signal and the other detected signal to produce an output signal having an amplitude proportional to the intensity of the emission line being monitored.

* * * * *